United States Patent
Knies et al.

(10) Patent No.: US 8,367,854 B2
(45) Date of Patent: Feb. 5, 2013

(54) METHOD FOR PRODUCING AND STABILIZING OLIGOAMINOSILANES

(75) Inventors: Wolfgang Knies, Burghausen (DE); Hans Eiblmeier, Burghausen (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 13/147,866

(22) PCT Filed: Feb. 11, 2010

(86) PCT No.: PCT/EP2010/051672
§ 371 (c)(1),
(2), (4) Date: Aug. 4, 2011

(87) PCT Pub. No.: WO2010/094610
PCT Pub. Date: Aug. 26, 2010

(65) Prior Publication Data
US 2011/0295032 A1    Dec. 1, 2011

(30) Foreign Application Priority Data
Feb. 23, 2009  (DE) .......................... 10 2009 001 088

(51) Int. Cl.
*C07F 7/10*    (2006.01)

(52) U.S. Cl. ...................................... 556/401; 556/413

(58) Field of Classification Search .................. 556/401, 556/413
See application file for complete search history.

(56) References Cited

U.S. PATENT DOCUMENTS

| | | | |
|---|---|---|---|
| 2,385,018 A | | 9/1945 | Milone |
| 5,621,061 A | * | 4/1997 | Hager et al. .................... 528/21 |
| 2004/0096582 A1 | | 5/2004 | Wang et al. |
| 2007/0099004 A1 | | 5/2007 | Edelmann et al. |
| 2010/0274028 A1 | * | 10/2010 | Mueh et al. .................... 549/215 |

FOREIGN PATENT DOCUMENTS

| DE | 10362060 A1 | 9/2005 |
|---|---|---|
| WO | 03045959 A1 | 6/2003 |

OTHER PUBLICATIONS

International Search Report for PCT/EP2010/051672 dated Jun. 16, 2010.

* cited by examiner

*Primary Examiner* — Johann Richter
*Assistant Examiner* — Pancham Bakshi
(74) *Attorney, Agent, or Firm* — Caesar, Rivise, Bernstein, Cohen & Pokotilow, Ltd.

(57) ABSTRACT

The invention relates to a method for producing oligoaminosilanes of the general formula (I) $Si_nY_{2n+2}$, wherein oligohalosilanes of the general formula (II) $Si_nX_{2n+2}$ are reacted with primary amines of the general formula (III) R—$NH_2$ in hydrocarbons as solvents, wherein X is selected from among chlorine, bromine, and iodine, Y is a halogen, hydrogen, or R—NH, R is a hydrocarbon group having 1 to 20 carbon atoms, and n is values from 1 to 20, with the stipulation that at most 35 mol % of the groups Y is a hydrogen and at most 15 mol % of the groups Y is a halogen, wherein activated carbon is added to the reaction mixture. The invention further relates to a method for stabilizing the oligoaminosilanes of the general formula (I), wherein the oligoaminosilanes are treated with activated carbon.

20 Claims, No Drawings

METHOD FOR PRODUCING AND STABILIZING OLIGOAMINOSILANES

BACKGROUND OF THE INVENTION

The invention relates to a process for preparing oligoaminosilanes from oligohalosilane and primary amine, wherein activated carbon is added to the reaction mixture, and to the stabilization of the oligoaminosilanes.

Aminosilane compounds are of great interest for the production of Si—N and Si—O layers. Amino-substituted monosilanes have already been investigated for this purpose, and some disilanes also exhibit good properties. In this respect, there is an interest in compounds with a high silicon content.

WO 03/045959 describes the preparation of hexakisethylaminodisilane from hexachlorodisilane and ethylamine in pentane. The hexakisethylaminodisilane thus prepared only has limited storage stability even with strict exclusion of water and air.

Since a high purity is required for the uses of oligoaminosilanes, such as hexakisethylaminodisilane, there is a high demand for products which do not have a tendency toward decomposition and hence contamination in the course of storage.

SUMMARY OF THE INVENTION

The invention provides a process for preparing oligoaminosilanes of the general formula (I)

$$Si_nY_{2n+2} \quad (I),$$

in which oligohalosilanes of the general formula (II)

$$Si_nX_{2n+2} \quad (II)$$

are reacted with primary amines of the general formula (III)

$$R—NH_2 \quad (III)$$

in hydrocarbons as a solvent,
where
X is selected from chlorine, bromine and iodine,
Y is halogen, hydrogen or R—NH,
R is a hydrocarbyl radical having 1 to 20 carbon atoms, and
n has values of 1 to 20,
with the proviso that at most 35 mol % of the Y radicals are hydrogen and
at most 15 mol % of the Y radicals are halogen,
wherein activated carbon is added to the reaction mixture.

The presence of the activated carbon in the preparation of the oligoaminosilanes of the general formula (I) distinctly enhances the storage stability of the oligoaminosilanes. It is also possible to improve the yield of oligoaminosilanes of the general formula (I). In addition, the chlorine content of the product is also reduced.

The activated carbon used in the process preferably contains at least 90% by weight of carbon. The BET surface area is preferably at least 200 m²/g, especially at least 400 m²g, of activated carbon. The activated carbon can be produced from vegetable, animal, mineral or petrochemical starting materials. The production is preferably accomplished by treatment of the starting materials with dehydrating agents, such as zinc chloride, sulfuric acid or phosphoric acid, at 500 to 900° C., or by dry distillation. The crude activated carbon thus obtained is subsequently oxidatively activated at 700 to 1000° C. with steam or carbon dioxide, or with air.

In the general formula (I), preferably at most 20 mol %, more preferably at most 10 mol %, especially none, of the Y radicals are hydrogen.

In the general formula (I), preferably at most 1 mol %, more preferably at most 0.1 mol %, especially at most 0.01 mol %, especially preferably none, of the Y radicals is halogen.

The halogen X and optionally Y is preferably chlorine.

R may especially be a linear or branched alkyl, cycloalkyl, aryl, alkenyl or arylalkyl radical. The R radical preferably has 1 to 12, especially 1 to 6, carbon atoms. Particularly preferred R radicals are methyl, ethyl, n-propyl, isopropyl, n-butyl, isobutyl, tert-butyl, n-pentyl, isopentyl, neopentyl or tert-pentyl radical and phenyl radical.

n preferably has values of 1 to 6, particular preference being given to the values of 1, 2, 3 or 4.

Preferred hydrocarbon solvents are solvents and solvent mixtures having a boiling point or boiling range of up to 120° C. at 1 bar. Examples of such solvents are the alkanes having 3 to 10 carbon atoms, aromatics having 6 to 12 carbon atoms, halogenated alkanes having 1 to 3 carbon atoms and mixtures thereof. Preferred examples are dichloromethane, tetrachloromethane, butane, pentane, hexane, heptane, octane, benzene, toluene and xylenes, and isomer mixtures thereof.

Preferentially prepared oligoaminosilanes of the general formula (I) are linear or branched. More preferentially prepared oligoaminosilanes of the general formula (I) are linear oligoaminosilanes of the general formula (IV)

$$Y(SiY_2)_mSiY_3 \quad (IV)$$

in which Y is as defined above and
m has the values of 1, 2, 3, 4 or 5.

Likewise preferentially prepared oligoaminosilanes of the general formula (I) are the oligoaminosilanes of the general formula (V)

$$Y_3Si(SiZ_2)SiY_3 \quad (V)$$

in which Y is as defined above and
Z is hydrogen, halogen or $SiY_3$.

Preference is given to using primary amine of the general formula (III) in excess compared to the oligohalosilane of the general formula (II). The excess of primary amine is preferably at least 1.1:1, more preferably at least 2:1 and especially at least 5:1, and preferably at most 20:1, based in each case on 1 mol of X groups in the oligohalosilane.

For each mole of X groups in the oligohalosilane, preferably at least 0.5 g, more preferably at least 2 g, and preferably at most 30 g, more preferably at most 10 g, of activated carbon are used.

In a preferred embodiment, the activated carbon is added to the reaction mixture after conversion of at least 50%, especially 75%, of the X groups in the oligohalosilane.

In a further preferred embodiment, the primary amine of the general formula (III) is initially charged in the solvent and the oligohalosilane of the general formula (II) is metered in. Preferably, the activated carbon is added after addition of the oligohalosilane. Particular preference is given to first removing the excess of amine and then adding the activated carbon.

The conversion temperature is preferably at least −80° C., more preferably at least −40° C., and preferably at most 100° C., more preferably at most 30° C.

The conversion pressure is preferably 0.5 bar, more preferably at least 1 bar, and preferably at most 10 bar. In the case of use of volatile primary amines, such as methylamine and ethylamine, the use of pressures of more than 1 bar may be advantageous.

Preferably, the activated carbon is filtered off in the course of workup of the reaction mixture.

The invention likewise provides a process for stabilizing oligoaminosilanes of the general formula (I), in which the oligoaminosilanes are admixed with activated carbon. For this purpose, preference is given to using activated carbon in piece form.

DETAILED DESCRIPTION OF PREFERRED EMBODIMENTS

All above symbols in the above formulae are each defined independently of one another. In all formulae, the silicon atom is tetravalent.

In the examples which follow, unless stated otherwise in each case, all amounts and percentages are based on weight, all pressures are 1 bar (abs.) and all temperatures are 20° C.

EXAMPLE 1

Preparation of Hexakisethylaminodisilane (Inventive)

1300 g of isohexane are introduced into a flask. 720 g of ethylamine are condensed into the isohexane. For this purpose, the solution is cooled to −40° C. Subsequently, 270 g of hexachlorodisilane are metered in while cooling such that the temperature does not exceed 0° C. After the metered addition has ended, the mixture is stirred for one hour and then the flask contents are transferred to a filter. Excess ethylamine and approx. 400 g of isohexane are distilled out of the solution obtained. For this purpose, a vacuum is applied, which is increased gradually to 400 mbar at a temperature of approx. 40° C. The concentrate now obtained (approx. 1100 g) is treated with 30 g of activated carbon while stirring for 10 hours. The activated carbon is filtered off and the concentrate is distilled. The hexakisethylaminodisilane target product distills over at top temperature 120° C. and 2.5 mbar.

EXAMPLE 2

Preparation of Hexakisethylaminodisilane (Noninventive)

1300 g of isohexane are introduced into a flask. 720 g of ethylamine are condensed into the isohexane. For this purpose, the solution is cooled to −40° C. Subsequently, 270 g of hexachlorodisilane are metered in while cooling such that the temperature does not exceed 0° C. After the metered addition has ended, the mixture is stirred for one hour and then the flask contents are transferred to a filter. The solution is subsequently distilled. For this purpose, the vacuum is gradually increased to 1-3 mbar at a temperature of 60° C. Thereafter, the temperature is increased again at 1-3 mbar. The hexakisethylaminodisilane target product distills over at top temperature 120° C. and 2.5 mbar.

Tests of the Products

The stability of the hexakisethylaminodisilane prepared according to examples 1 and 2 is tested by heating approx. 5 g of substance in a screw-secured steel tube at 150° C. The percentage decrease in the hexakisethylaminodisilane is:

|  | 1 day/150° C. | 5 days/150° C. |
|---|---|---|
| Product from example 2* | −24% | −53% |
| Product from example 1 | −4% | −23% |

*noninventive

The inventive treatment with activated carbon also increases the yield. The yield over all fractions is:

| Product from example 2 (noninventive) | 77% |
|---|---|
| Product from example 1 | 82% |

The inventive procedure also reduces the chlorine content of the product. It is, measured by ion chromatography:

| Product from example 2 (noninventive) | 25 ppm |
|---|---|
| Product from example 1 | 13 ppm |

The invention claimed is:

1. A process for preparing oligoaminosilanes of the general formula (I)

$$Si_nY_{2n+2} \quad (I),$$

in which an oligohalosilane of the general formula (II)

$$Si_nX_{2n+2} \quad (II)$$

is reacted with a primary amine of the general formula (III)

$$R-NH_2 \quad (III)$$

in a reaction mixture in hydrocarbons as a solvent,
where
X is selected from chlorine, bromine and iodine,
Y is halogen, hydrogen or R—NH,
R is a hydrocarbyl radical having 1 to 20 carbon atoms, and
n has values of 1 to 20,
   with the proviso that at most 35 mol % of Y radicals are hydrogen and at most 15 mol % of the Y radicals are halogen,
   wherein activated carbon is added to the reaction mixture.

2. The process as claimed in claim 1, in which R is an alkyl radical having 1 to 6 carbon atoms.

3. The process as claimed in claim 1, in which linear oligoaminosilanes of the general formula (IV)

$$Y(SiY_2)_mSiY_3 \quad (IV)$$

are prepared, where
m has the values of 1, 2, 3, 4 or 5.

4. The process as claimed in claim 1, in which oligoaminosilanes of the general formula (V)

$$Y_3Si(SiZ_2)SiY_3 \quad (V)$$

are prepared, where
Z is hydrogen, halogen or $SiY_3$.

5. The process as claimed in claim 1, in which the primary amine of the general formula (III) is used in excess compared to the oligohalosilane of the general formula (II).

6. The process as claimed in claim 5, in which the activated carbon is added to the reaction mixture after conversion of at least 75% of the X groups in the oligohalosilane.

7. The process as claimed in claim 1, in which the primary amine of the general formula (III) is initially charged in the solvent and the oligohalosilane of the general formula (II) is metered in and, after addition of the oligohalosilane, the activated carbon is added.

8. The process as claimed in claim 1, in which a conversion temperature is −80° C. to 100° C.

9. A process for stabilizing oligoaminosilanes of the general formula (I):

$$Si_nY_{2n+2} \quad (I),$$

where
Y is halogen, hydrogen or R—NH,
R is a hydrocarbyl radical having 1 to 20 carbon atoms, and
n has values of 1 to 20,
with the proviso that at most 35 mol % of Y radicals are hydrogen and
at most 15 mol % of the Y radicals are halogen, said process comprising admixing the oligoaminosilanes with activated carbon.

10. The process as claimed in claim 2, in which linear oligoaminosilanes of the general formula (IV)

are prepared, where
m has the values of 1, 2, 3, 4 or 5.

11. The process as claimed in claim 2, in which oligoaminosilanes of the general formula (V)

are prepared, where
Z is hydrogen, halogen or $SiY_3$.

12. The process as claimed in claim 2, in which the primary amine of the general formula (III) is used in excess compared to the oligohalosilane of the general formula (II).

13. The process as claimed in claim 3, in which the primary amine of the general formula (III) is used in excess compared to the oligohalosilane of the general formula (II).

14. The process as claimed in claim 4, in which the primary amine of the general formula (III) is used in excess compared to the oligohalosilane of the general formula (II).

15. The process as claimed in claim 2, in which the primary amine of the general formula (III) is initially charged in the solvent and the oligohalosilane of the general formula (II) is metered in and, after addition of the oligohalosilane, the activated carbon is added.

16. The process as claimed in claim 3, in which the primary amine of the general formula (III) is initially charged in the solvent and the oligohalosilane of the general formula (II) is metered in and, after addition of the oligohalosilane, the activated carbon is added.

17. The process as claimed in claim 4, in which the primary amine of the general formula (III) is initially charged in the solvent and the oligohalosilane of the general formula (II) is metered in and, after addition of the oligohalosilane, the activated carbon is added.

18. The process as claimed in claim 2, in which a conversion temperature is −80° C. to 100° C.

19. The process as claimed in claim 3, in which a conversion temperature is −80° C. to 100° C.

20. The process as claimed in claim 4, in which a conversion temperature is −80° C. to 100° C.

* * * * *